US012765844B2

(12) United States Patent
Langoju et al.

(10) Patent No.: US 12,765,844 B2
(45) Date of Patent: Oct. 20, 2026

(54) METHOD AND SYSTEMS FOR ALIASING ARTIFACT REDUCTION IN COMPUTED TOMOGRAPHY IMAGING

(71) Applicant: GE Precision Healthcare LLC, Waukesha, WI (US)

(72) Inventors: Rajesh Langoju, Bengaluru (IN); Utkarsh Agrawal, Bengaluru (IN); Risa Shigemasa, Hino (JP); Bipul Das, Bengaluru (IN); Yasuhiro Imai, Hino (JP); Jiang Hsieh, Brookfield, WI (US)

(73) Assignee: GE Precision Healthcare LLC, Waukesha, WI (US)

( * ) Notice: Subject to any disclaimer, the term of this patent is extended or adjusted under 35 U.S.C. 154(b) by 163 days.

(21) Appl. No.: 18/929,269

(22) Filed: Oct. 28, 2024

(65) Prior Publication Data

US 2025/0049400 A1 Feb. 13, 2025

Related U.S. Application Data

(63) Continuation of application No. 17/444,881, filed on Aug. 11, 2021, now Pat. No. 12,156,752.

(51) Int. Cl.

*A61B 6/02* (2006.01)
*G06N 3/04* (2023.01)

(Continued)

(52) U.S. Cl.

CPC ................. *A61B 6/02* (2013.01); *G06N 3/04* (2013.01); *G06N 3/08* (2013.01); *G06T 3/4076* (2013.01);

(Continued)

(58) Field of Classification Search

CPC .......... A61B 6/02; A61B 6/5258; G06N 3/08; G06N 3/045; G06N 3/0464; G06N 3/09; G06N 3/084; G06T 3/4076; G06T 12/10; G06T 12/30; G06T 15/08; G06T 12/20; G06T 2211/441; G06T 5/60; G06T 5/70; G06T 2207/10081; G06T 2207/20081; G06T 2207/20084; G01T 1/2985; G01N 23/046

(Continued)

(56) References Cited

U.S. PATENT DOCUMENTS

| | | | | |
|---|---|---|---|---|
| 2018/0374245 | A1* | 12/2018 | Xu | A61B 6/032 |
| 2020/0193656 | A1* | 6/2020 | Schoendube | A61B 6/032 |
| 2022/0058438 | A1* | 2/2022 | Prince | G06F 18/2148 |

* cited by examiner

*Primary Examiner* — Jennifer Mehmood
*Assistant Examiner* — Dustin Bilodeau

(57) ABSTRACT

Various methods and systems are provided for computed tomography imaging. In one embodiment, a method includes acquiring, with an x-ray detector and an x-ray source coupled to a gantry, a three-dimensional image volume of a subject while the subject moves through a bore of the gantry and the gantry rotates the x-ray detector and the x-ray source around the subject, inputting the three-dimensional image volume to a trained deep neural network to generate a corrected three-dimensional image volume with a reduction in aliasing artifacts present in the three-dimensional image volume, and outputting the corrected three-dimensional image volume. In this way, aliasing artifacts caused by sub-sampling may be removed from computed tomography images while preserving details, texture, and sharpness in the computed tomography images.

20 Claims, 9 Drawing Sheets

(51) Int. Cl.

| | |
|---|---|
| ***G06N 3/08*** | (2023.01) |
| ***G06T 3/4076*** | (2024.01) |
| ***G06T 12/10*** | (2026.01) |
| ***G06T 12/30*** | (2026.01) |
| ***G06T 15/08*** | (2011.01) |
| *G06T 12/20* | (2026.01) |

(52) U.S. Cl.
CPC .............. *G06T 12/10* (2026.01); *G06T 12/30* (2026.01); *G06T 15/08* (2013.01); *G06T 12/20* (2026.01); *G06T 2211/441* (2023.08)

(58) Field of Classification Search
USPC .......................................................... 382/131
See application file for complete search history.

METHOD AND SYSTEMS FOR ALIASING ARTIFACT REDUCTION IN COMPUTED TOMOGRAPHY IMAGING

CROSS-REFERENCE TO RELATED APPLICATIONS

The present matter is a continuation of and claims priority to U.S. patent application Ser. No. 17/444,881, filed Aug. 11, 2021, the contents of which are incorporated by reference herein.

FIELD

Embodiments of the subject matter disclosed herein relate to computed tomography imaging systems, and more particularly, to correcting aliasing artifacts in computed tomography images.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures).

BRIEF DESCRIPTION

In one embodiment, a method comprises acquiring, with an x-ray detector and an x-ray source coupled to a gantry, a three-dimensional image volume of a subject while the subject moves through a bore of the gantry and the gantry rotates the x-ray detector and the x-ray source around the subject, inputting the three-dimensional image volume to a trained deep neural network to generate a corrected three-dimensional image volume with a reduction in aliasing artifacts present in the three-dimensional image volume, and outputting the corrected three-dimensional image volume. In this way, aliasing artifacts caused by sub-sampling may be removed from computed tomography images while preserving details, texture, and sharpness in the computed tomography images.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 4:
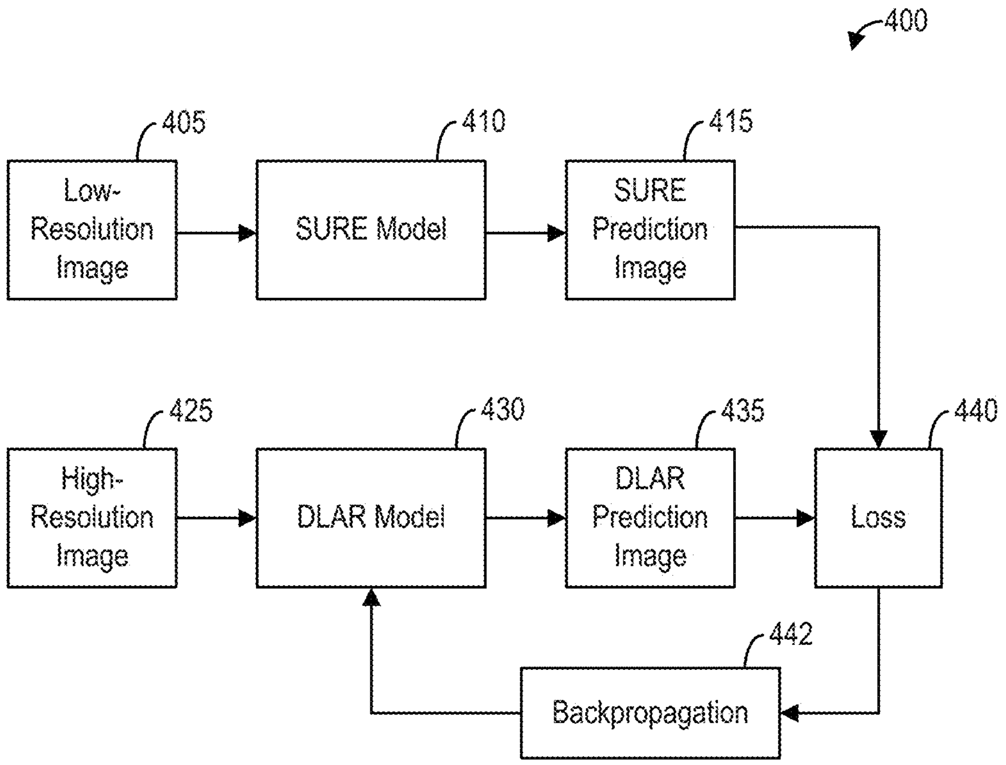
FIG. 4 shows a block diagram illustrating an exemplary deep learning system for training a deep learning model for artifact reduction, according to an embodiment.
Figure 5:
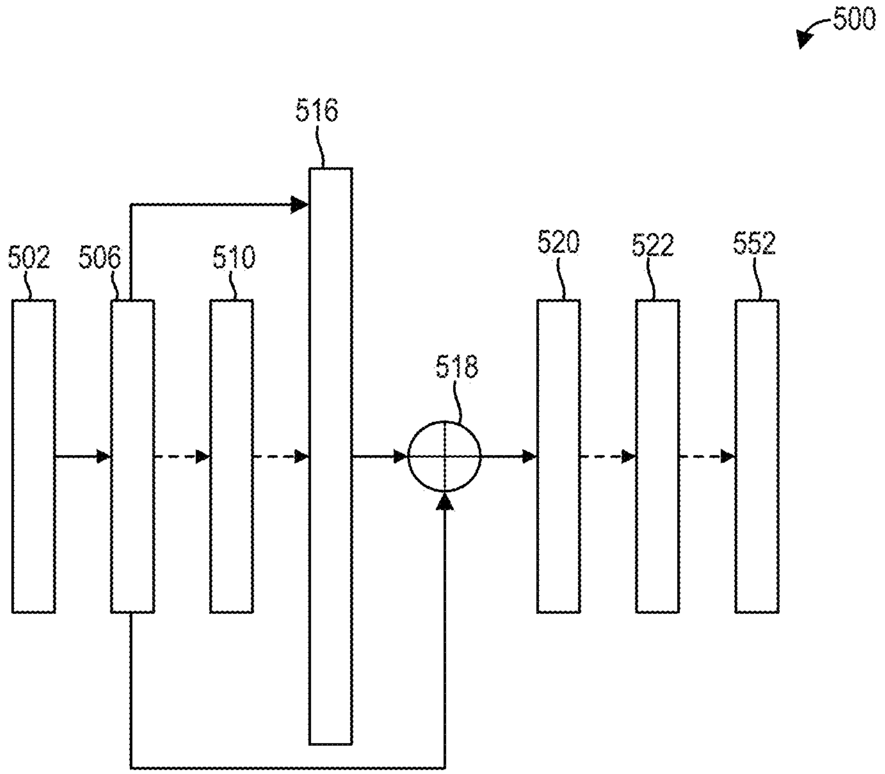
FIG. 5 shows a block diagram illustrating an exemplary architecture for a deep neural network configured to generate ground truth images for training a deep learning model for artifact reduction, according to an embodiment.
Figure 6:
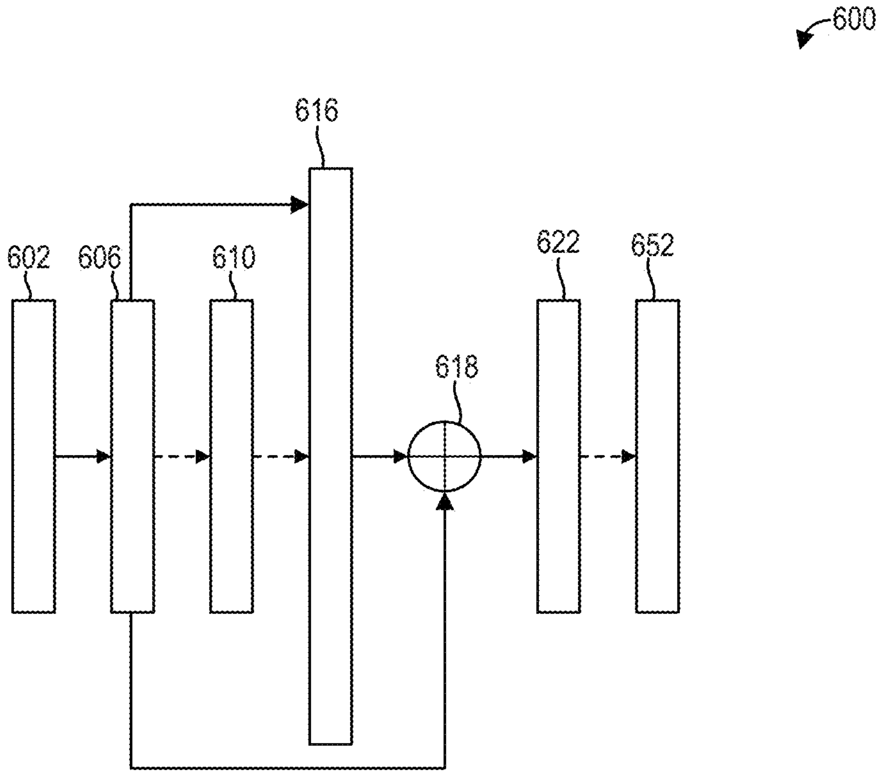
FIG. 6 shows a block diagram illustrating an exemplary architecture for a deep learning neural network configured for artifact reduction, according to an embodiment.
Figure 7:
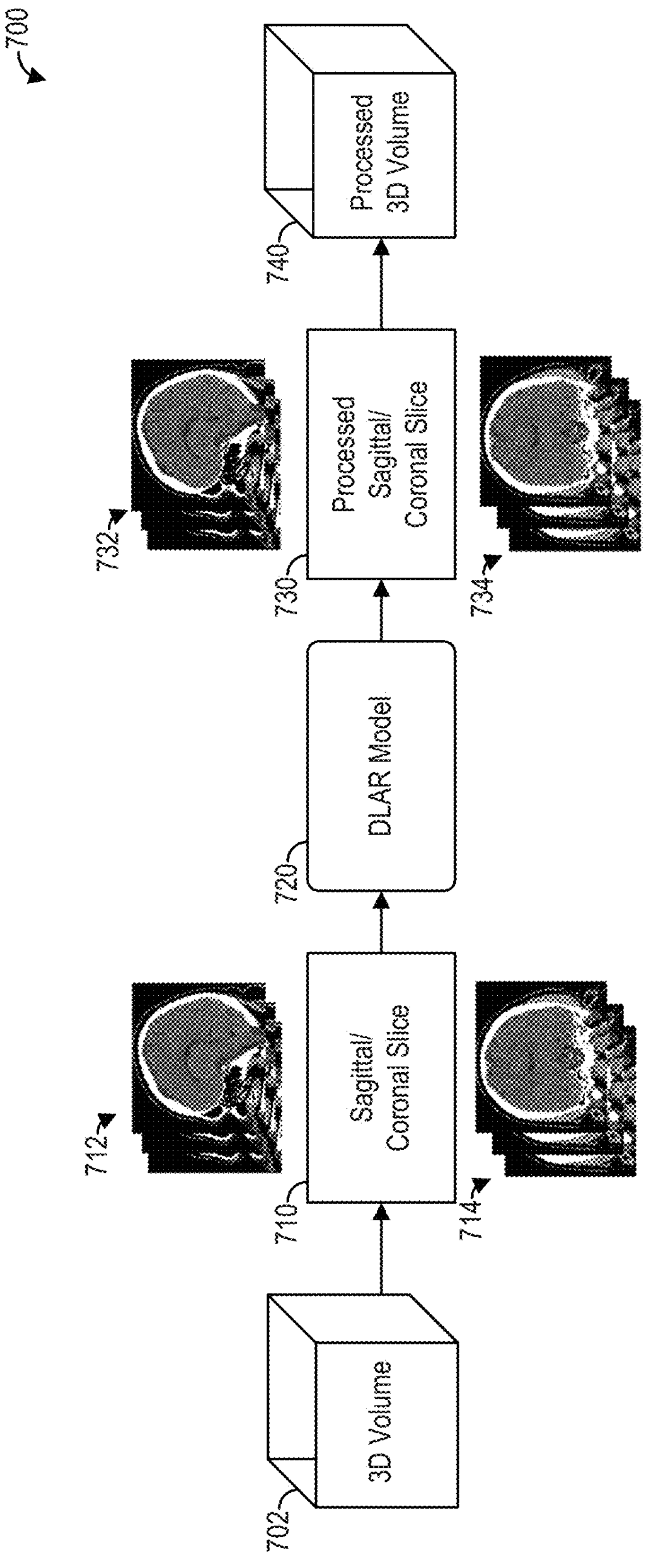
FIG. 7 shows a block diagram illustrating an example method for artifact reduction with a trained deep learning model, according to an embodiment.
Figure 8:
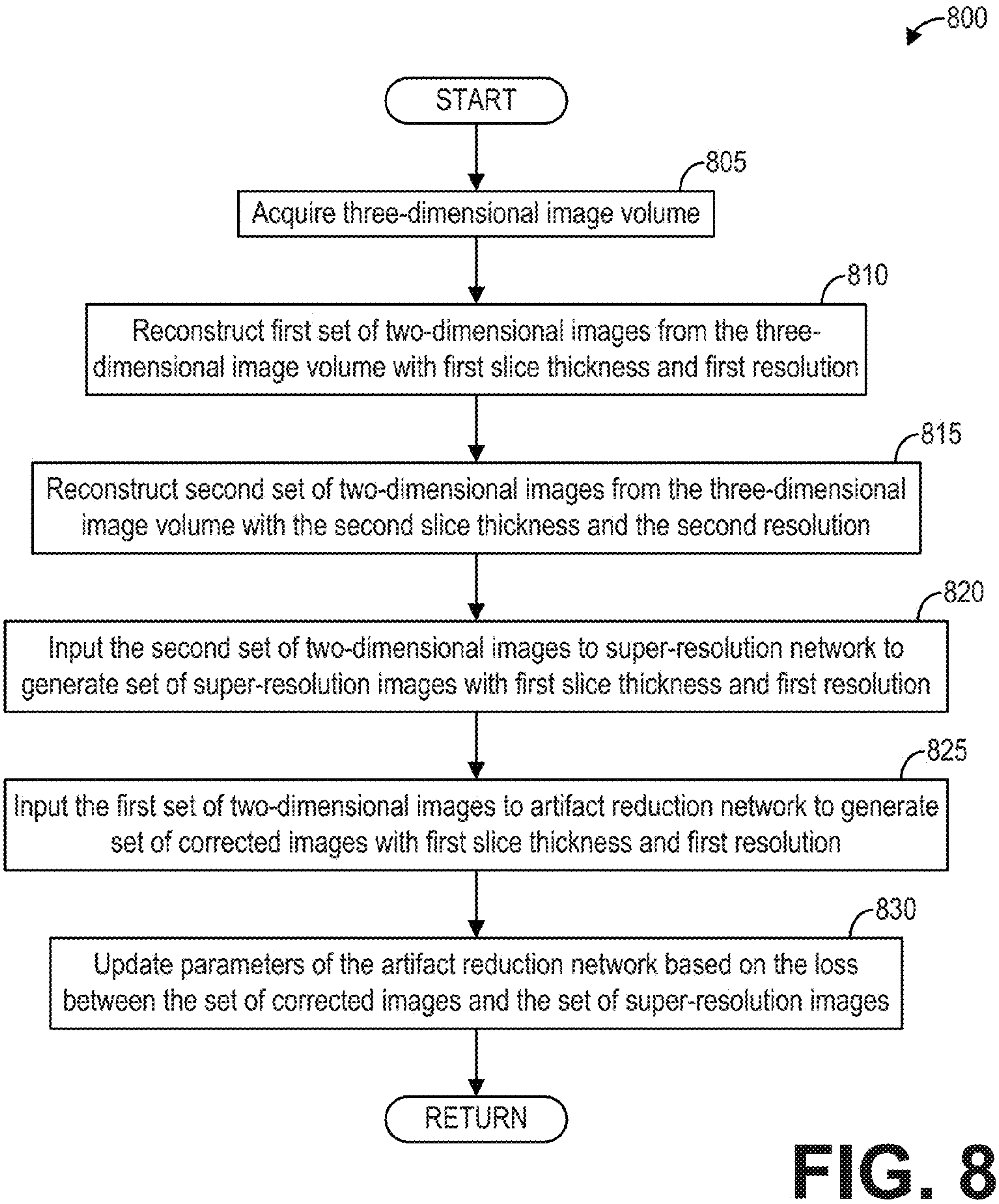
FIG. 8 shows a high-level flow chart illustrating an example method for training a deep learning model for artifact reduction, according to an embodiment.
Figure 9:
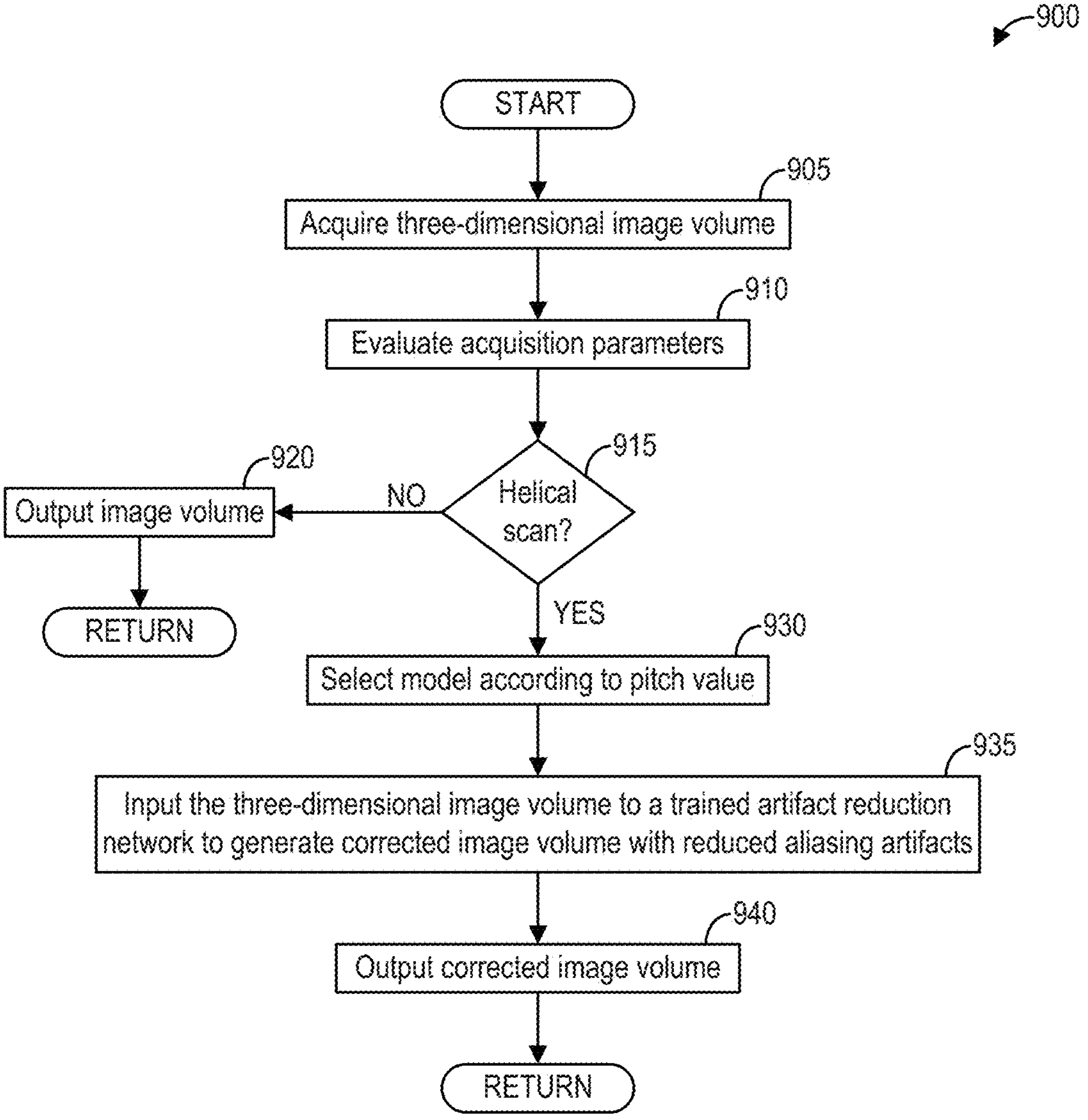
FIG. 9 shows a high-level flow chart illustrating an example method for correcting aliasing artifacts in three-dimensional image volumes.
Figure 10:
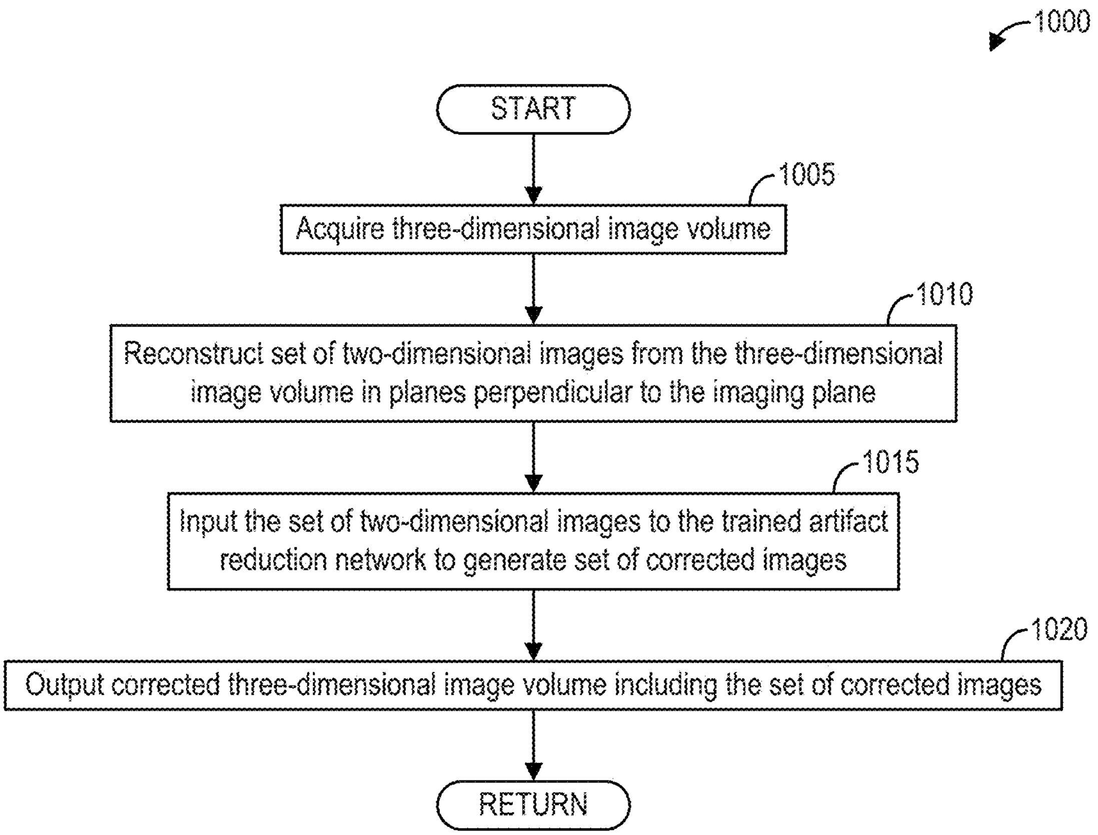
FIG. 10 shows a high-level flow chart illustrating an example method for correcting artifacts with a trained deep learning model, according to an embodiment.

The following description relates to various embodiments of computed tomography (CT) imaging. In particular, systems and methods for removing aliasing artifacts in CT imaging are provided. When imaging a subject such as a patient with a CT imaging system, such as the CT imaging system depicted in FIGS. 1 and 2, the subject may be moved through a gantry bore while an x-ray source and x-ray detector mounted on a gantry rotate about the subject. Due to this motion of the subject through the imaging system, aliasing artifacts may arise in reconstructed images due to sub-sampling. An image processing system, such as the image processing system depicted in FIG. 3, may include one or more deep neural networks configured to automatically remove such aliasing artifacts from acquired images. In order to train a deep neural network to reduce aliasing artifacts, a training system as depicted in FIG. 4 may include a super-resolution neural network configured to generate ground truth images without aliasing artifacts. The super-resolution neural network and the aliasing artifact reduction neural network, as depicted in FIGS. 5 and 6 respectively, may comprise convolutional neural networks. Once trained, the aliasing artifact reduction neural network may process two-dimensional slices in directions perpendicular to the gantry plane or imaging plane to remove aliasing artifacts, as depicted in FIG. 7. A method for training an aliasing artifact reduction neural network is depicted in FIG. 8, and methods for and correcting image volumes with an aliasing artifact reduction neural network are depicted in FIGS. 9 and 10.

Figure 1:
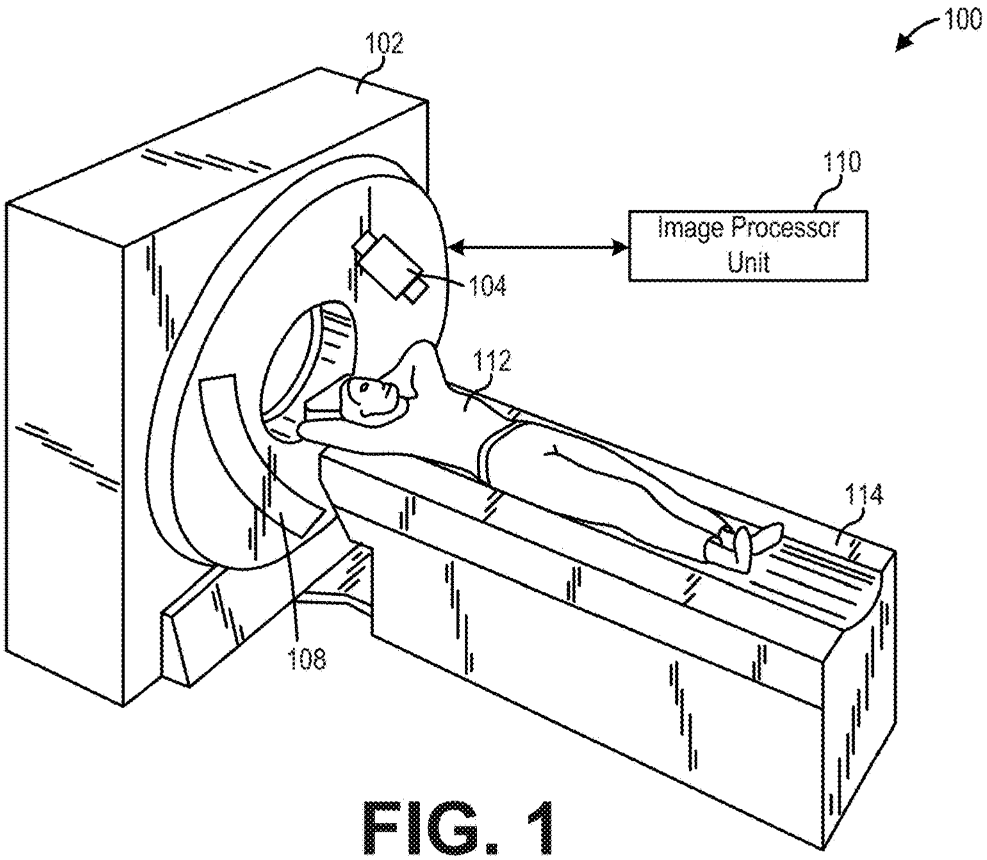
FIG. 1 shows a pictorial view of an exemplary medical imaging system, according to an embodiment.

Referring now to FIG. 1, an exemplary imaging system 100 is depicted according to an embodiment. In the illustrated embodiment, the imaging system 100 is an X-ray imaging system configured to perform CT imaging. Though the illustrated embodiment actively acquires medical images, it is understood that other embodiments do not actively acquire medical images. Instead, embodiments may retrieve images or imaging data that was previously acquired by an imaging system and process the imaging data as set forth herein.

The imaging system 100 may be configured to image a subject 112 such as a patient, an inanimate object, one or more manufactured parts, and/or foreign objects such as dental implants, stents, and/or contrast agents present within the body. In one embodiment, the imaging system 100 may include a gantry 102, which in turn, may further include at least one X-ray source 104 configured to project a beam of X-ray radiation 106 (see FIG. 2) for use in imaging the subject 112 laying on a table 114. Specifically, the X-ray source 104 may be configured to project the X-rays 106 towards a detector array 108 positioned on the opposite side of the gantry 102. Although FIG. 1 depicts a curved detector array 108, in certain embodiments, a flat-panel detector may be employed. Further, although FIG. 1 depicts a single X-ray source 104, in certain embodiments, multiple X-ray sources and/or detectors may be employed to project a plurality of X-ray radiation beams 106 for acquiring projection data corresponding to the subject 112 at different energy levels or angular orientations. In some CT imaging embodiments, the X-ray source 104 may enable dual-energy imaging by rapid peak kilovoltage (kVp) switching. In some embodiments, the X-ray detector employed is a photon-counting detector which is capable of differentiating X-ray photons of different energies. In other embodiments, two sets of X-ray sources and detectors are used to generate dual-energy projections, with one set acquired at a low-kVp setting and the other acquired at a high-kVp setting. It should thus be appreciated that the methods described herein may be implemented with single energy acquisition techniques as well as dual energy acquisition techniques.

In certain embodiments, the imaging system 100 further includes an image processor unit 110 configured to reconstruct images of a target volume of the subject 112 using an iterative or analytic image reconstruction method, or a combination of both. For example, in some CT imaging applications, the image processor unit 110 may use an analytic image reconstruction approach such as filtered backprojection (FBP) to reconstruct images of a target volume of the patient. As another example, the image processor unit 110 may use an iterative image reconstruction approach such as advanced statistical iterative reconstruction (ASIR) or model-based iterative reconstruction (MBIR), and the like, to reconstruct images of a target volume of the subject 112. In some examples, the image processor unit 110 may use both an analytic image reconstruction approach such as FBP in addition to an iterative image reconstruction approach. In one embodiment, and as discussed in detail below, the image processor unit 110 may use an iterative image reconstruction approach leveraging one-dimensional homographic resampling transforms.

In some CT imaging system configurations, an X-ray source projects a cone-shaped X-ray radiation beam which is collimated to lie within an X-Y-Z plane of a Cartesian coordinate system (generally referred to as an "imaging plane"). The X-ray radiation beam passes through an object being imaged, such as the patient or subject. The X-ray radiation beam, after being attenuated by the object, impinges upon an array of radiation detectors. The intensity of the attenuated X-ray radiation beam received at the detector array is dependent upon the attenuation of an X-ray radiation beam by the object. Each detector element of the array produces a separate electrical signal that is a measurement (e.g., a line integral measurement) of the X-ray beam attenuation at the detector location. The attenuation measurements from all the detector elements are acquired separately to produce a transmission profile.

In some CT imaging systems, the X-ray source and the detector array are rotated with a gantry about the imaging plane and around the object to be imaged such that an angle at which the radiation beam intersects the object constantly changes. A group of X-ray radiation attenuation measurements, e.g., projection data, from the detector array at one angular position of the gantry is referred to as a "view." A "scan" of the object includes a set of views made at different angular positions, or view angles, during one revolution of the X-ray source and detector about the object. It is contemplated that the benefits of the methods described herein accrue to many medical imaging modalities, so as used herein the term "view" is not limited to the use as described above with respect to projection data from one gantry angle. The term "view" is used to mean one data acquisition whenever there are multiple data acquisitions from different angles, whether from a CT, X-ray radiographic imaging, positron emission tomography (PET), or single-photon emission CT (SPECT) acquisition, and/or any other modality including modalities yet to be developed as well as combinations thereof in fused embodiments.

The projection data is processed to reconstruct an image that corresponds to one or more two-dimensional slices taken through the object or, in some examples where the projection data includes extended axial coverage, e.g., Z-axis illumination, a three-dimensional image volume of the object. One method for reconstructing an image from a set of projection data is referred to in the art as the filtered backprojection technique. Transmission and emission tomography reconstruction techniques also include statistical iterative methods such as maximum likelihood expectation maximization (MLEM) and ordered-subsets expectation maximization reconstruction techniques as well as iterative reconstruction techniques. This process converts the attenuation measurements from a scan into integers (called "CT numbers" or "Hounsfield units" in the case of a CT imaging system), which are used to control the brightness of a corresponding pixel on a display device.

To reduce the total scan time, a "helical" scan may be performed. To perform a "helical" scan, the patient is moved while the data for the prescribed axial coverage is acquired. Such a system generates a single helix from a cone-beam helical scan. The helix mapped out by the cone beam yields projection data from which images in each prescribed slice may be reconstructed.

As used herein, the phrase "reconstructing an image" is not intended to exclude embodiments of the present disclosure in which data representing an image is generated but a viewable image is not. Therefore, as used herein, the term "image" broadly refers to both viewable images and data representing a viewable image. However, many embodiments generate (or are configured to generate) at least one viewable image.

Figure 2:
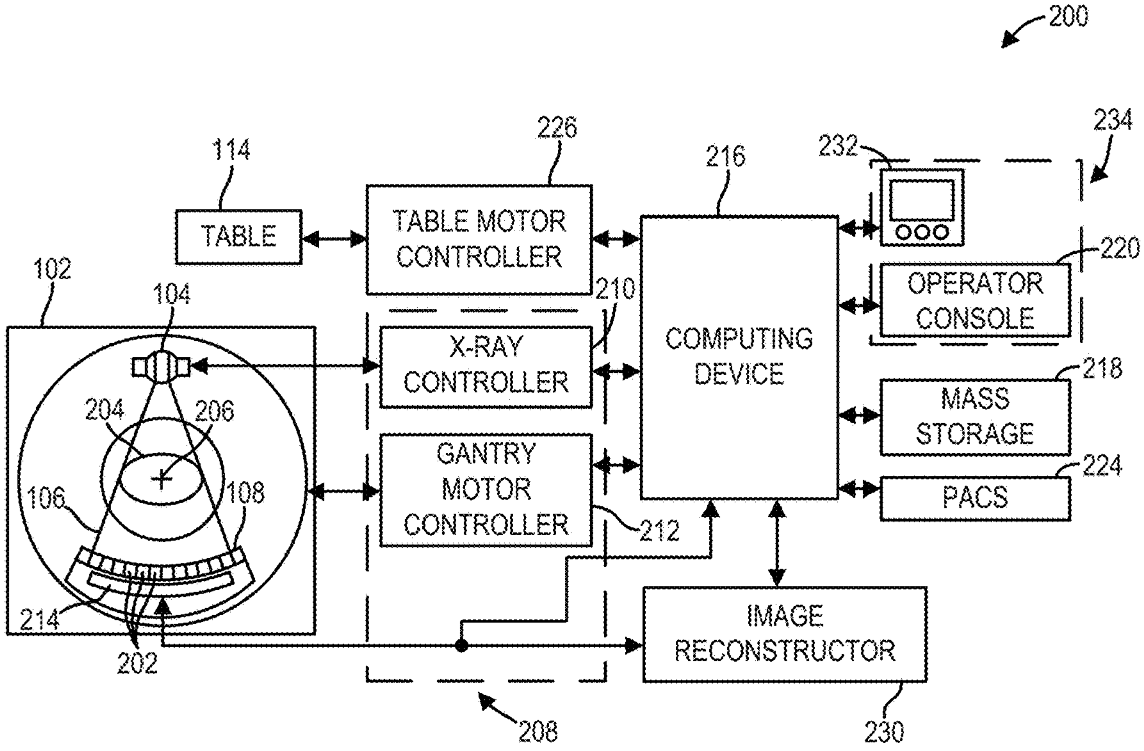
FIG. 2 shows a block diagram of the exemplary medical imaging system, according to an embodiment.

Referring now to FIG. 2, an exemplary imaging system 200 similar to the imaging system 100 of FIG. 1 is depicted. As shown, the imaging system 200 may include multiple components. The components may be coupled to one another to form a single structure, may be separate but located within a common room, or may be remotely located with respect to one another. For example, one or more of the modules described herein may operate in a data server that has a distinct and remote location with respect to other components of the imaging system 200.

In accordance with aspects of the present disclosure, the imaging system 200 may be configured for imaging a subject 204 (e.g., the subject 112 of FIG. 1). In one embodiment, the imaging system 200 may include the detector array 108 (see FIG. 1). The detector array 108 may further include a plurality of detector elements 202 that together sense the X-ray radiation beams 106 that pass through the subject 204 (such as a patient) to acquire corresponding projection data. Accordingly, in one embodiment, the detector array 108 may be fabricated in a multi-slice configuration including the plurality of rows of cells or detector elements 202. In such a configuration, one or more additional rows of the detector elements 202 may be arranged in a parallel configuration for acquiring the projection data.

The gantry 102 may movably support the X-ray source 104 and the detector array 108 mounted opposite to each other on opposed ends. The subject 204 may accordingly be disposed between the X-ray source 104 and the detector array 108, supported by the table 114.

It will be recognized that in some embodiments, the table 114 may further be movable to achieve a desired image acquisition. During such an acquisition of image data, the gantry 102 may be movable to change a position and/or orientation of the X-ray source 104 and/or the detector array 108 relative to the subject 204.

Accordingly, in some embodiments, the gantry 102 may remain fixed during a given imaging session so as to image a single 2D projection of the subject 204. In such embodiments, a position of the gantry 102 and/or the table 114 may be adjusted between imaging sessions so as to image another view of the subject 204.

In other embodiments, such as in CT imaging applications, the imaging system 200 may be configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

In such embodiments, as the X-ray source 104 and the detector array 108 rotate, the detector array 108 may collect data of the attenuated X-ray beams. The data collected by the detector array 108 may undergo preprocessing and calibration to condition and process the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections may be converted to a set of material-density projections. The material-density projections may be reconstructed to form a pair or a set of material-density maps or images of each respective basis material, such as bone, soft tissue, and/or contrast agent maps. The material-density maps or images may be, in turn, associated to form a volume rendering of the basis material, for example, bone, soft tissue, and/or contrast agent, in the imaged volume.

Once reconstructed, the basis material image produced by the imaging system 200 may reveal internal features of the subject 204, expressed in the densities of two basis materials. The density image, or combinations of multiple density images, may be displayed to show these features. In traditional approaches to diagnosis of medical conditions, such as disease states, and more generally of medical events, a radiologist or physician would consider a hard copy or display of the density image, or combinations thereof, to discern characteristic features of interest. Such features might include lesions, sizes and shapes of particular anatomies or organs, and other features that would be discernable in the image based upon the skill and knowledge of the individual practitioner.

In one embodiment, the imaging system 200 may include a control mechanism 208 to control movement of the components such as rotation of the gantry 102 and the operation of the X-ray source 104. In certain embodiments, the control mechanism 208 may further include an X-ray controller 210 configured to provide power and timing signals to the X-ray source 104. Additionally, the control mechanism 208 may include a gantry motor controller 212 configured to control a rotational speed and/or position of the gantry 102 or of various components thereof (e.g., the X-ray source 104, the detector array 108, etc.) based on imaging requirements.

In certain embodiments, the control mechanism 208 may further include a data acquisition system (DAS) 214 configured to sample analog data received from the detector elements 202 and convert the analog data to digital signals for subsequent processing. For photon-counting imaging systems, the DAS 214 may download measured photon counts in one or more energy bins from detector array 108. The DAS 214 may further be configured to selectively aggregate analog data from a subset of the detector elements 202 into so-called macro-detectors, as described further herein.

The data sampled and digitized by the DAS 214 may be transmitted to a computer or computing device 216. In the illustrated embodiment, the computing device 216 may be configured to interface with various components of the imaging system 200. As such, the computing device 216 may be configured to control operation of the imaging system 200. In various embodiments, the computing device 216 may take the form of a mainframe computer, server computer, desktop computer, laptop computer, tablet device, network computing device, mobile computing device, mobile communication device, etc. In one embodiment, the computing device 216 may take the form of an edge device for interfacing between the various components of FIG. 2. In some embodiments, the one or more components of the imaging system 200 configured to acquire X-ray radiation may be considered an X-ray imaging subsystem (e.g., the X-ray source 104, the detector array 108, etc.) of the overall imaging system 200, which may be a computing system further configured to interface with a user and perform a variety of computational processes (e.g., imaging or non-imaging). Accordingly, other components (e.g., the computing device 216, etc.) of the imaging system 200 may be communicably coupled to the X-ray imaging subsystem.

In some embodiments, the computing device 216 may store the data in a storage device or mass storage 218, either included in the computing device 216 (in such examples, the computing device 216 may be referred to as a controller) or a separate device communicably coupled to the computing device 216 (in such examples, the computing device 216 may be referred to as a processor). The storage device 218 may include removable media and/or built-in devices. Specifically, the storage device 218 may include one or more physical, non-transitory devices configured to hold data and/or instructions executable by the computing device 216 to implement the herein described methods. Accordingly, when such methods are implemented, a state of the storage device 218 may be transformed (for example, to hold different, or altered, data). The storage device 218, for example, may include magnetoresistive random-access memory (MRAM), a hard disk drive, a floppy disk drive, a tape drive, a compact disk-read/write (CD-R/W) drive, a Digital Versatile Disc (DVD) drive, a high-definition DVD (HD-DVD) drive, a Blu-Ray drive, a flash drive, and/or a solid-state storage drive. It will be appreciated that the storage device 218 may be a non-transitory storage medium.

Additionally, the computing device 216 may provide commands and parameters to one or more of the DAS 214, the X-ray controller 210, and the gantry motor controller 212 for controlling system operations such as data acquisition and/or processing. In certain embodiments, the computing device 216 controls system operations based on operator input, e.g., via a user interface 234. The computing device 216 receives the operator input, for example, including commands and/or scanning parameters via an operator console 220 operatively coupled to the computing device 216. The operator console 220 may include a physical keyboard, mouse, touchpad, and/or touchscreen to allow the operator to specify the commands and/or scanning parameters.

Although FIG. 2 illustrates only one operator console 220, more than one operator console 220 may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 may either include, or may be coupled to, a picture archiving and communications system (PACS) 224. In an exemplary implementation, the PACS 224 may further be coupled to a remote system such as radiological information systems (e.g., RIS), electronic health or medical records and/or hospital information systems (e.g., EHR/HIS), and/or to an internal or external network (not shown) to allow operators at different locations to supply commands and parameters and/or gain access to the image data.

The computing device 216 may use the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized X-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. For example, one embodiment may use computing resources in a "cloud" network cluster for the image reconstructor 230.

In one embodiment, the image reconstructor 230 may store the images reconstructed in the storage device 218, either via the computing device 216 as shown in FIG. 2 or via a direct connection (not shown). Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

The various methods or processes (such as the method described below with reference to FIG. 7) described further herein may be stored as executable instructions in non-transitory memory on a computing device (or controller), or in communication with a computing device (or processor), in the imaging system 200. In one embodiment, the image reconstructor 230 may include such executable instructions in non-transitory memory, and may apply the methods described herein to reconstruct an image from scanning data. In another embodiment, the computing device 216 may include the instructions in non-transitory memory, and may apply the methods described herein, at least in part, to a reconstructed image after receiving the reconstructed image from the image reconstructor 230. In yet another embodiment, the methods and processes described herein may be distributed across the image reconstructor 230 and the computing device 216.

In operation, the computing device 216 may acquire imaging data and other medical data, which may be translated for display to a user (e.g., a medical professional) via the user interface 234, for example, on the display device 232. As an example, the medical data may be transformed into and displayed at the display device 232 as a user-facing graphical and/or textual format, which may be standardized across all implementations of the imaging system 200 or may be particular to a given facility, department, profession, or individual user. As another example, the imaging data (e.g., three-dimensional (3D) volumetric data sets, two-dimensional (2D) imaging slices, etc.) may be used to generate one or more images at the computing device 216, which may then be displayed to the operator or user at the display device 232. As such, the display device 232 may allow the operator to evaluate the imaged anatomy. The display device 232 may also allow the operator to select a volume of interest (VOI) and/or request patient information, for example, via a graphical user interface (GUI) for a subsequent scan or processing.

Figure 3:
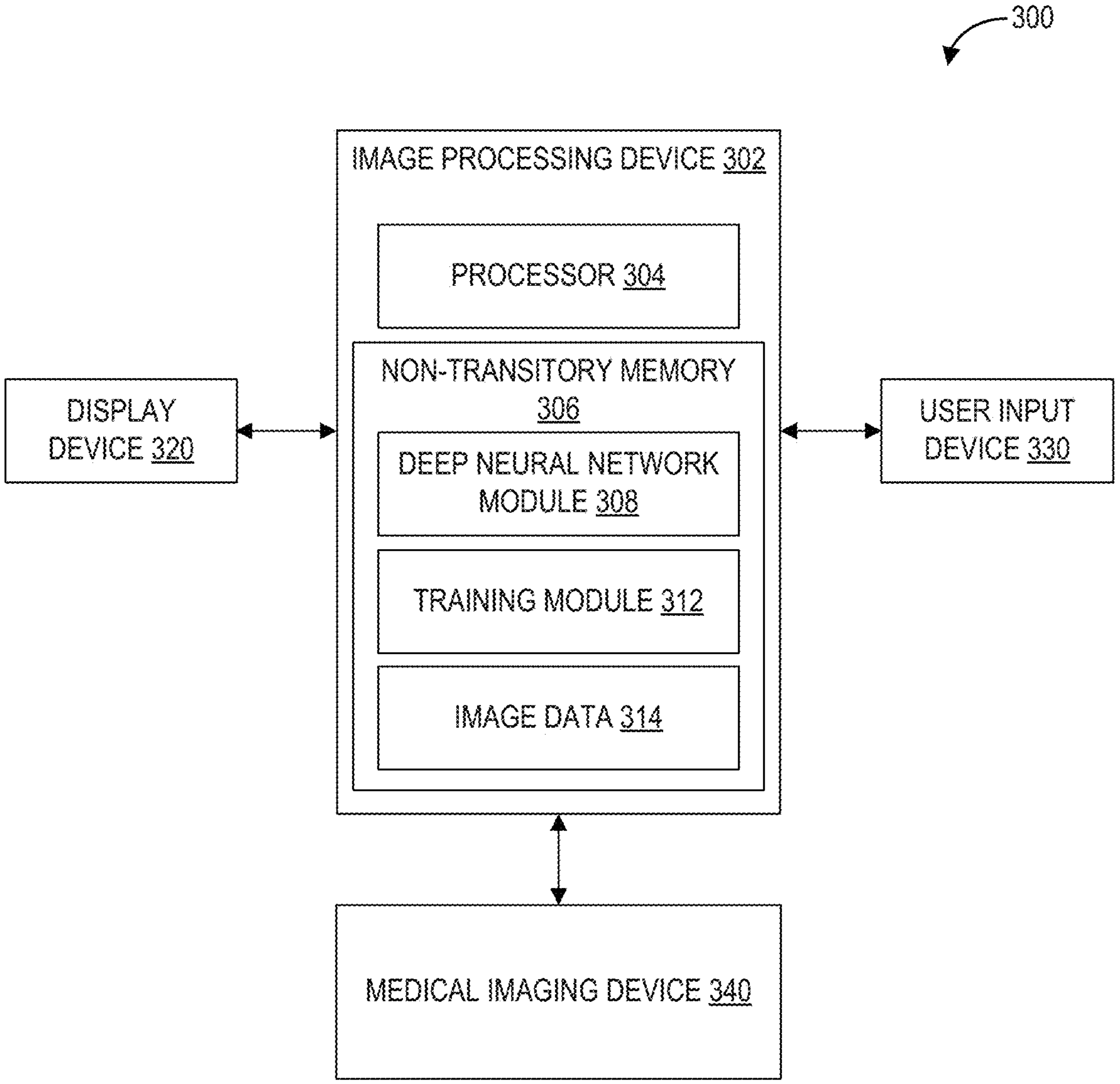
FIG. 3 shows a block diagram of an exemplary medical image processing system, according to an embodiment.

Referring to FIG. 3, a medical image processing system 300 is shown, in accordance with an exemplary embodiment. Medical image processing system 300 comprises image processing device 302, display device 320, user input device 330, and medical imaging device 340. In some embodiments, at least a portion of medical image processing system 300 is disposed at a remote device (e.g., edge device, server, etc.) communicably coupled to the medical imaging system 300 via wired and/or wireless connections. In some embodiments, at least a portion of image processing device 302 is disposed at a separate device (e.g., a workstation)

configured to receive images from a storage device which stores images acquired by medical imaging device 340.

Image processing device 302 includes a processor 304 configured to execute machine readable instructions stored in non-transitory memory 306. Processor 304 may be single core or multi-core, and the programs executed thereon may be configured for parallel or distributed processing. In some embodiments, the processor 304 may optionally include individual components that are distributed throughout two or more devices, which may be remotely located and/or configured for coordinated processing. In some embodiments, one or more aspects of the processor 304 may be virtualized and executed by remotely-accessible networked computing devices configured in a cloud computing configuration.

Non-transitory memory 306 may store deep neural network module 308, training module 312, and image data 314. Deep neural network module 308 may include one or more deep neural networks, comprising a plurality of weights and biases, activation functions, and instructions for implementing the one or more deep neural networks to reduce aliasing artifacts due to sub-sampling. For example, deep neural network module 308 may store instructions for implementing one or more deep neural networks configured to reduce aliasing artifacts in CT images. An example deep neural network configured for aliasing artifact reduction is described further herein with regard to FIG. 6. The deep neural network module 308 may further include one or more deep neural networks configured to generate ground truth images for training the artifact reduction neural network(s) by simulating a reduced artifact image from a thick slice image through super-resolution in the axial direction and/or planes perpendicular to the imaging plane. An example deep neural network configured for generating such ground truth images is described further herein with regard to FIG. 5.

Deep neural network module 308 may include trained and/or un-trained deep neural networks. In some embodiments, the deep neural network module 308 is not disposed at the image processing device 302, but is disposed at a remote device communicably coupled with image processing device 302 via wired or wireless connection. Deep neural network module 308 may include various deep neural network metadata pertaining to the trained and/or un-trained networks. In some embodiments, the deep neural network metadata may include an indication of the training data used to train a deep neural network, a training method employed to train a deep neural network, and an accuracy/validation score of a trained deep neural network. In some embodiments, deep neural network module 308 may include metadata for a trained deep neural network indicating a type of anatomy, and/or a type of imaging modality, to which the trained deep neural network may be applied.

Non-transitory memory 306 further includes training module 312, which comprises machine executable instructions for training one or more of the deep neural networks stored in deep neural network module 308. In one embodiment, the training module 312 may include gradient descent algorithms, loss functions, and rules for generating and/or selecting training data for use in training a deep neural network. Training module 312 may further include instructions, that when executed by processor 104, cause image processing device 302 to train a deep neural network with a bias-reducing loss function by executing one or more of the operations of method 800, discussed in more detail below with reference to FIG. 8. In some embodiments, the training module 312 is not disposed at the image processing device 302, but is disposed remotely, and is communicably coupled with image processing device 302. An example architecture for training a deep neural network with the training module 312 is described further herein with regard to FIG. 4.

Non-transitory memory 306 may further store image data 314, comprising medical images/imaging data acquired by medical imaging device 340. Image data 314 may further comprise medical images/imaging data received from other medical imaging systems, via communicative coupling with the other medical imaging systems. The medical images stored in image data 314 may comprise medical images from various imaging modalities or from various models of medical imaging devices, and may comprise images of various views of anatomical regions of one or more patients. In some embodiments, medical images stored in image data 314 may include information identifying an imaging modality and/or an imaging device (e.g., model and manufacturer of an imaging device) by which the medical image was acquired. As described herein, image data 314 may comprise CT images captured by a CT imaging system. It should be appreciated that in some embodiments, image data 314 may comprise x-ray images acquired by an x-ray device, MR images captured by an MRI system, CT images captured by a CT imaging system, PET images captures by a PET system, and/or one or more additional types of medical images.

In some embodiments, the non-transitory memory 306 may include components disposed at two or more devices, which may be remotely located and/or configured for coordinated processing. In some embodiments, one or more aspects of the non-transitory memory 306 may include remotely-accessible networked storage devices configured in a cloud computing configuration.

Medical image processing system 300 further includes medical imaging device 340, which may comprise a CT imaging system such as the imaging system 200. It should be appreciated that the medical imaging device 340 may comprise substantially any type of medical imaging device, including x-ray, MRI, CT, PET, hybrid PET/MR, ultrasound, etc. Imaging device 340 may acquire measurement data of an anatomical region of a patient, which may be used to generate medical images. The medical images generated from measurement data acquired by medical imaging device 340 may comprise two-dimensional (2D) or three-dimensional (3D) imaging data, wherein said imaging data may comprise a plurality of pixel intensity values (in the case of 2D medical images) or voxel intensity values (in the case of 3D medical images). The medical images acquired by medical imaging device 340 may comprise gray scale, or color images, and therefore the medical images stored in image data 314 may comprise a single color channel for gray scale images, or a plurality of color channels for colored medical images.

Medical image processing system 300 may further include user input device 330. User input device 330 may comprise one or more of a touchscreen, a keyboard, a mouse, a trackpad, a motion sensing camera, or other device configured to enable a user to interact with and manipulate data within image processing device 302.

Display device 320 may include one or more display devices utilizing virtually any type of technology. In some embodiments, display device 320 may comprise a computer monitor configured to display medical images of various types and styles. Display device 320 may be combined with processor 304, non-transitory memory 306, and/or user input device 330 in a shared enclosure, or may be a peripheral display device and may comprise a monitor, touchscreen, projector, or other display device known in the art, which may enable a user to view medical images having improved structural details while maintaining textural cues for the radiologist according to one or more embodiments of the current disclosure, and/or interact with various data stored in non-transitory memory 306.

It should be understood that medical image processing system 300 shown in FIG. 3 is for illustration, not for limitation. Another appropriate medical imaging system 300 may include more, fewer, or different components.

FIG. 4 shows a block diagram illustrating an exemplary deep learning system 400 for training a deep learning model for artifact reduction, according to an embodiment. The deep learning system 400 includes a super-resolution (SURE) model 400 and a deep learning artifact reduction (DLAR) model 430, as depicted. A low-resolution image 405 with a second slice thickness and a high-resolution image 425 with a first slice thickness smaller than the second slice thickness are reconstructed from the same projection dataset. The low-resolution image 405 is input to the SURE model 410 to obtain a SURE prediction image 415 comprising a super-resolution prediction image corresponding to the low-resolution image 405. The SURE model 410 is trained for super-resolution using axial data between a thick slice and a thin slice along the sagittal/coronal direction. In other words, the SURE model 410 generates an image of slice spacing z mm from an input image 405 of slice spacing 2z mm. By using a thicker slice spacing for the input image 405, the input image 405 is less affected by sub-sampling. Thus, the SURE model 410 is configured to increase the resolution of the input image 405 rather than reduce aliasing artifacts in the input image 405.

The high-resolution image 425 is input to the DLAR model 430 to obtain an artifact-corrected image or DLAR prediction image 435. Due to the high-resolution or slice thickness of the high-resolution image 425, the high-resolution image 425 includes aliasing artifacts while the DLAR prediction image 435 comprises the high-resolution image 425 with the aliasing artifacts removed or reduced. The high-resolution image(s) 425 comprise two-dimensional slices along the sagittal and coronal directions as aliasing is a result of sampling along the direction of the system axis. By operating in the direction of sub-sampling, the DLAR model 430 behaves as a match filter and learns only the uncorrelated high-frequency components, and so the DLAR model 430 is resilient to data variations for display field of view (DFOV), reconstruction kernel, and anatomy. Thus, the DLAR model 430 identifies the high-frequency components corresponding to aliasing and corrects only those high-frequency components, thus preserving the details, texture, and sharpness in the corrected image while completely or at least partially removing the aliasing artifacts.

The SURE prediction image 415 is used as the ground truth for training the DLAR model 430. To that end, loss 440 is determined between the SURE prediction image 415 and the DLAR prediction image 435, and backpropagation 442 is performed to update the weights and biases of the DLAR model 430, as an illustrative example. The loss function for loss 440 may comprise a mean absolute error (MAE) loss function in some examples, though it should be appreciated that other loss functions such as structural similarity index measure (SSIM) may be used without departing from the scope of the present disclosure.

Once trained, the DLAR model 430 may be used for inferencing. That is, once trained, the DLAR model 430 is configured to take two-dimensional slices with aliasing artifacts and generate two-dimensional slices with reduced aliasing artifacts. The DLAR model 430 depends on the nature of sampling, which impacts the frequency characteristics due to aliasing. For CT images, the sampling corresponds directly to the pitch for helical scans as well as detector characteristics.

It should be appreciated that the approach provided herein for generating ground truth images with the SURE model 410 is illustrative and non-limiting, and that the ground truth images may be generated with other approaches, including but not limited to simulation and/or measurement (e.g., wobbling z-focal-spot). For example, the ground truth images may be generated through hardware approaches that enhance the spatial resolution of the low-resolution images, including but not limited to focal spot wobble. Thus, ground truth images may be generated through one or more of hardware-based processing or software-based processing methods.

As an illustrative example of the SURE model 410, FIG. 5 shows a block diagram illustrating an exemplary architecture for a deep neural network 500 configured to generate ground truth images for training a deep learning model for artifact reduction, according to an embodiment. In particular, the deep neural network 500 may comprise a super-resolution (SURE) neural network configured to convert an input 502 comprising an image of second slice thickness and second resolution (i.e., a low-resolution image) into an output 552 comprising an image of first slice thickness and first resolution (i.e., a high-resolution image). For example, the second slice thickness may be greater than the first slice thickness, which corresponds to the second resolution being lower than the first resolution. In this way, by generating a corresponding image with a smaller slice thickness, the deep neural network 500 increases the image resolution.

As mentioned hereinabove, the input 502 of the deep neural network 500 comprises an image with a second slice thickness or a thick slice thickness. The slice thickness and slice spacing may comprise, as an illustrative and non-limiting example, 1.25 mm and 0.625 mm, respectively. The input 502 is input to a convolutional block layer 506 of the deep neural network 500 which performs shallow feature selection. The dashed line output of the convolutional block layer 506 indicates that one or more additional layers, such as one or more additional convolutional block layers, may be arranged in series after the convolutional block layer 506. The output of the one or more convolutional block layer(s) 506 is input to a residual dense block (RDB) 510. The dashed line output of the RDB 510 indicates that a plurality of RDBs may be arranged in series after the RDB 510. In some examples, the deep neural network 500 may include thirteen RDBs including the RDB 510 arranged in series, though it should be appreciated that the deep neural network 500 may include more or fewer RDBs without departing from the scope of the present disclosure.

The output of the convolutional block layer 506 and the output of the RDB 510 are combined at a concatenation layer 516. For global residual learning, the output of the concatenation layer 516 and the output of the convolutional block layer 506 are then provided to the global residual learning layer 518.

The output of the global residual learning layer 518 is then provided to an upsample layer 520 for upsampling, where the dashed line output of the upsample layer 520 indicates that one or more additional layers may be arranged in series after the upsample layer 520. The output of the upsample layer 520 and the one or more layers thereafter are input to a convolutional block layer 522, where the dashed line output of the convolutional block layer 522 indicates that one or more additional layers may be arranged in series after the convolutional block layer 522. The output of the convolutional block layer 522 and the one or more additional layers is the output 552 comprising an image of first slice thickness and first resolution. As an illustrative and non-limiting example, if the second slice thickness and second slice spacing of the input 502 is 1.25 mm and 0.625 mm, respectively, the first slice thickness and first slice spacing of the output 552 is 0.625 mm and 0.3125 mm, respectively. In other words, the deep neural network 500 may reduce the slice thickness and slice spacing of an input 502 by half with a resulting and corresponding increase in image resolution, as an illustrative and non-limiting example.

FIG. 6 shows a block diagram illustrating an exemplary architecture for a deep learning neural network 600 configured for artifact reduction, according to an embodiment. In particular, the deep neural network 600 may comprise a DLAR neural network configured to convert an input 602 comprising an image including aliasing artifacts into an output 652 comprising an image with reduced aliasing artifacts.

The input 602 of the deep neural network 600 comprises an image with the first slice thickness (i.e., the thin slice relative to the thick slice input to the SURE model 410 or the deep neural network 500). The input 602 is input to a convolutional block layer 606 of the deep neural network 600 which performs shallow feature selection. The dashed line output of the convolutional block layer 606 indicates that one or more additional layers may be arranged in series after the convolutional block layer 606. The output of the convolutional block layer 606 and the one or more additional layers is then input to an RDB 610. The dashed line output of the RDB 610 indicates that a plurality of RDBs may be arranged in series after the RDB 610. In some examples, the deep neural network 600 may include six RDBs including the RDB 610 arranged in series, though it should be appreciated that the deep neural network 600 may include more or fewer RDBs without departing from the scope of the present disclosure.

The output of the convolutional block layer 606, and the output of the RDB 610 are combined at a concatenation layer 616 for dense feature fusion. For global residual learning, the output of the concatenation layer 616 and the output of the convolutional block layer 606 for shallow feature selection are then provided to the global residual learning layer 618.

The output of the global residual learning layer 618 is then provided to a series of tail convolutional layers, including a convolutional block layer 622. The dashed line output of the convolutional block layer 622 indicates that one or more additional layers may be arranged in series after the convolutional block layer 622. The output of the tail convolutional layers including the convolutional block layer 622 is the output 652 comprising an image with reduced aliasing artifacts. In contrast with the output 552 of the deep neural network 500, the slice thickness of the output 652 comprises the same slice thickness as the input 602 (i.e., the first slice thickness).

FIG. 7 shows a block diagram illustrating an example method 700 for artifact reduction with a trained deep learning model such as the deep neural network 600. A three-dimensional (3D) volume 702 containing aliasing artifacts is arranged into sagittal/coronal slices 710 including a plurality of sagittal slices 712 and a plurality of coronal slices 714 for processing. The sagittal/coronal slices 710 are input to the trained DLAR model 720 which outputs processed sagittal/coronal slices 730 including a plurality of processed sagittal slices 732 and a plurality of processed coronal slices 734. The processed sagittal/coronal slices 730 are then output as a processed 3D volume 740 which corresponds to the 3D volume 702 with reduced aliasing artifacts.

Although the method 700 depicts two-dimensional (2D) processing of the three-dimensional image volume 702 to perform aliasing corrections, it should be appreciated that the trained deep neural network may be configured to perform two-dimensional (2D), two-and-a-half-dimensional (2.5D), or three-dimensional (3D) processing of the three-dimensional image volume 702 to filter image data of the three-dimensional image volume 702 along directions perpendicular to an imaging plane formed by the x-ray detector and the x-ray source, such as the sagittal and coronal planes in examples wherein the imaging plane is aligned with the axial plane.

FIG. 8 shows a high-level flow chart illustrating an example method 800 for training a deep learning model for artifact reduction, according to an embodiment. Method 800 is described with regard to the systems and components of FIGS. 1-6, though it should be appreciated that the method 800 may be implemented with other systems and components without departing from the scope of the present disclosure. Method 800 may be implemented as executable instructions in non-transitory memory 306, for example, and may be executed by the processor 304 to perform the actions described herein. Further, method 800 may be implemented in the training module 312 for training a deep neural network to reduce aliasing artifacts caused by sub-sampling.

Method 800 begins at 805. At 805, method 800 acquires a three-dimensional image volume. Method 800 acquires the three-dimensional image volume during a helical scan of a subject, for example, wherein a gantry rotates an x-ray detector and an x-ray source about a subject while the subject travels through a bore of the gantry.

At 810, method 800 reconstructs a first set of two-dimensional images from the three-dimensional image volume with a first slice thickness and a first resolution. The first slice thickness may comprise a desired slice thickness of reconstructed images, wherein aliasing artifacts may arise due to sub-sampling of acquired data relative to the desired slice thickness. Further, at 815, method 800 reconstructs a second set of two-dimensional images from the three-dimensional image volume with a second slice thickness and a second resolution, where the second slice thickness is larger than the first slice thickness such that the sub-sampling error and resulting aliasing artifacts do not occur. The slices of the first set of two-dimensional images and the second set of two-dimensional images may be aligned, such that each slice of the first set of two-dimensional images corresponds to a slice of the second set of two-dimensional images, aside from the differences in slice thickness.

At 820, method 800 inputs the second set of two-dimensional images to a super-resolution network to generate a set of super-resolution images with the first slice thickness and the first resolution. That is, the super-resolution neural network, which may comprise the super-resolution neural network 500 for example, transforms each image of the second set of two-dimensional images with the second slice thickness to a super-resolution image with the first slice thickness. As the images of the second set of two-dimensional images do not include aliasing artifacts due to the thicker slice thickness, the super-resolution images similarly do not include aliasing artifacts despite the transformation in slice thickness.

At 825, method 800 inputs the first set of two-dimensional images to an artifact reduction neural network to generate a set of corrected images with the first slice thickness and the first resolution. The artifact reduction neural network, which may comprise the neural network 600 for example, processes the first set of two-dimensional images to reduce aliasing artifacts in the two-dimensional images.

At 830, method 800 updates parameters of the artifact reduction neural network based on the loss between the set of corrected images and the set of super-resolution images. Specifically, method 800 determines a loss according to a difference between the set of corrected images and the set of super-resolution images. The weights and biases of the artifact reduction neural network are then updated via back-propagation according to the loss. It should be appreciated that while method 800 is described with regard to one three-dimensional imaging volume, during training of the artifact reduction neural network, a training dataset comprising a plurality of three-dimensional image volumes may be used to generate respective sets of two-dimensional slices for each three-dimensional image volume. By updating the artifact reduction neural network in this way with a training dataset comprising a plurality of three-dimensional image volumes and minimizing the loss during training, the artifact reduction neural network is thus trained to reduce aliasing artifacts. After updating the parameters of the artifact reduction neural network to minimize loss between the corrected images and the ground truth images, method 800 returns.

FIG. 9 shows a high-level flow chart illustrating an example method 900 for correcting aliasing artifacts in three-dimensional image volumes with a trained deep learning model, according to an embodiment. Method 900 is described with regard to the systems and components of FIGS. 1-6, though it should be appreciated that the method 900 may be implemented with other systems and components without departing from the scope of the present disclosure. Method 900 may be implemented as executable instructions in non-transitory memory 306 and may be executed by the processor 304 to perform the actions described herein, as an illustrative and non-limiting example.

Method 900 begins at 905. At 905, method 900 acquires a three-dimensional image volume. For example, method 900 may acquire the three-dimensional image volume by controlling a medical imaging device 340 such as the imaging system 200 to acquire the three-dimensional image volume. As another example, method 900 may retrieve a three-dimensional image volume stored in non-transitory memory as image data 314, for example, wherein the three-dimensional image volume was previously acquired by a medical imaging device 340 such as the imaging system 200.

Further, at 910, method 900 evaluates acquisition or imaging parameters for acquiring the three-dimensional image volume. The acquisition or imaging parameters may include, as illustrative and non-limiting examples, a type of scan (e.g., helical scan, axial scan, and so on), gantry rotation speed, table speed, reconstruction kernel, slice thickness, x-ray source parameters, x-ray detector parameters, and so on.

Method 900 may determine whether to perform aliasing artifact correction based on the acquisition parameters. For example, at 915, method 900 may determine whether the acquisition comprised a helical scan. If the acquisition does not comprise a helical scan ("NO"), then aliasing artifacts may not be present in the three-dimensional image volume because there is no relative motion between the subject and the imaging plane, and so method 900 proceeds to 920. At 920, method 900 outputs the three-dimensional image volume without performing any aliasing artifact corrections. Method 900 then returns.

However, referring again to 915, if the acquisition comprises a helical scan ("YES"), method 900 proceeds to 930. At 930, method 900 may select a model according to a pitch value comprising the value of the helical pitch (e.g., the speed of the table 114 and the rotation of the gantry 102). For example, a plurality of deep neural networks may each be trained for a respective helical pitch value. After selecting the model based on the pitch value, method 900 proceeds to 935.

At 935, method 900 inputs the three-dimensional image volume to a trained artifact reduction neural network to generate a corrected image volume with reduced aliasing artifacts. The trained artifact reduction neural network may comprise the model selected at 930, for example. Method 900 may input the three-dimensional image volume to the deep learning artifact reduction model 430, for example, which may comprise the deep learning neural network 600 trained as described hereinabove with regard to FIGS. 4 and 8. As described further herein with regard to FIG. 10, inputting the three-dimensional image volume to the trained artifact reduction neural network may include reconstructing two-dimensional slices in planes perpendicular to the imaging plane, and inputting the two-dimensional slices to the trained artifact reduction neural network to obtain corrected two-dimensional slices with aliasing artifacts reduced. As aliasing artifacts may not arise in the imaging plane, which may comprise the axial plane for clinical scans of subjects moving through the gantry bore directly along the z axis perpendicular to the imaging plane or gantry plane (i.e., without a tilt or angle between the gantry and the subject). In such examples wherein the imaging plane or gantry plane comprises the axial plane for reconstruction, the two-dimensional slices are reconstructed in the sagittal and coronal planes. However, for non-clinical scans where an axial plane is not defined or for scans wherein the gantry is tilted relative to the subject moving through the gantry bore (i.e., such that the direction of travel of the subject is not directly aligned with the z axis), the imaging plane is not in the x-y plane but has a z component, so the two-dimensional slices are reconstructed in a first plane and a second plane perpendicular to the imaging plane wherein aliasing artifacts arise. In other words, regardless of the relative orientation of the gantry, the subject, and a fixed coordinate system, aliasing artifacts arise in planes perpendicular to the imaging plane of the gantry and so the two-dimensional slices are reconstructed in the planes perpendicular to the imaging plane. In other examples, the three-dimensional image volume may be processed as a volume rather than slice by slice. For example, the three-dimensional image volume may be directly input to a trained artifact reduction neural network configured with filters to process the three-dimensional image volume for aliasing artifact reduction along aliasing directions.

At 940, method 900 outputs the corrected image volume. The corrected image volume includes the corrected two-dimensional slices for slice processing, or the corrected three-dimensional image volume for volume processing. Method 900 outputs the corrected image volume, for example to one or more of a display device such as display device 320, non-transitory memory such as image data 314 of non-transitory memory 306, or another module for additional processing of the corrected image volume such as other artifact corrections, segmentation, reconstruction, and so on. Method 900 then returns.

FIG. 10 shows a high-level flow chart illustrating an example method 1000 for correcting artifacts with a trained deep learning model, according to an embodiment. In particular, method 1000 relates to processing a three-dimensional image volume slice-by-slice to reduce aliasing artifacts in the three-dimensional image volume. Method 1000 is described with regard to the systems and components of FIGS. 1-6, though it should be appreciated that the method 1000 may be implemented with other systems and components without departing from the scope of the present disclosure. Method 1000 may be implemented as executable instructions in non-transitory memory 306, for example, and may be executed by the processor 304 to perform the actions described herein. Further, method 1000 may be implemented in the deep neural network module 308 for reducing aliasing artifacts caused by sub-sampling of the medical imaging device 340.

Method 1000 begins at 1005. At 1005, method 1000 acquires a three-dimensional image volume. Acquiring the three-dimensional image volume may comprise, for example, controlling a medical imaging device 340 such as the imaging system 200 to acquire a three-dimensional image volume. As another example, method 1000 may retrieve the three-dimensional image volume from image data 314 of non-transitory memory 306.

At 1010, method 1000 reconstructs a set of two-dimensional images from the three-dimensional image volume in planes perpendicular to the imaging plane. For example, if the imaging plane is aligned with the axial plane of the three-dimensional image volume, method 1000 reconstructs two-dimensional slices in the sagittal and coronal planes which are perpendicular to the axial plane and thus to the imaging plane. For scans wherein the imaging plane does not comprise the axial plane due to gantry tilt or a non-clinical subject, for example, method 1000 reconstructs two-dimensional slices in a first plane perpendicular to the imaging plane and a second plane perpendicular to the imaging plane. The two-dimensional images may include aliasing artifacts caused by sub-sampling of the acquisition of the three-dimensional image volume relative to the slice thickness of the two-dimensional images. The slice thickness of the two-dimensional images may be thin enough that sufficient projection data is not included to avoid sub-sampling and so aliasing artifacts are present in the two-dimensional images. For example, the slice thickness of the two-dimensional images may be below the slice thickness threshold described hereinabove with regard to FIG. 9. It should be appreciated that the slice spacing of the two-dimensional images or slices may vary for different examples without departing from the scope of the present disclosure. For example, aliasing artifacts may occur in each two-dimensional slice due to the amount of data used to generate the two-dimensional slice and such artifacts arise independent of an amount of overlap between neighboring slices or a distance between neighboring slices due to a selected slice spacing.

At 1015, method 1000 inputs the set of two-dimensional images to the trained artifact reduction neural network to generate a set of corrected images. The trained artifact reduction neural network comprises, for example, the deep neural network 600 trained as described hereinabove with regard to FIGS. 4 and 8. The corrected images output by the trained artifact reduction neural network exhibit a reduction in aliasing artifacts. At 1020, method 1000 outputs the corrected three-dimensional image volume including the set of corrected images. Method 1000 then returns.

A technical effect of the disclosure includes a reduction of aliasing artifacts in computed tomography images. Another technical effect of the disclosure includes the removal of aliasing artifacts in computed tomography images while preserving details, texture, and sharpness in the computed tomography images. Yet another technical effect of the disclosure includes the display of high-resolution computed tomography images without aliasing artifacts caused by sub-sampling.

In one embodiment, a method comprises acquiring, with an x-ray detector and an x-ray source coupled to a gantry, a three-dimensional image volume of a subject while the subject moves through a bore of the gantry and the gantry rotates the x-ray detector and the x-ray source around the subject, inputting the three-dimensional image volume to a trained deep neural network to generate a corrected three-dimensional image volume with a reduction in aliasing artifacts present in the three-dimensional image volume, and outputting the corrected three-dimensional image volume.

In a first example of the method, the method further comprises performing, with the trained deep neural network, two-dimensional processing of the three-dimensional image volume to filter image data of the three-dimensional image volume along directions perpendicular to an imaging plane formed by the x-ray detector and the x-ray source. In a second example of the method optionally including the first example, inputting the three-dimensional image volume to the trained deep neural network to generate the corrected three-dimensional image volume comprises reconstructing a plurality of two-dimensional images from the three-dimensional image volume along planes perpendicular to the imaging plane formed by the x-ray detector and the x-ray source, inputting the plurality of two-dimensional images to the trained deep neural network to generate a plurality of corrected two-dimensional images, and generating the corrected three-dimensional image volume from the plurality of corrected two-dimensional images. In a third example of the method optionally including one or more of the first and second examples, the method further comprises reconstructing the plurality of two-dimensional images with a first slice thickness, wherein the aliasing artifacts present in the plurality of two-dimensional images arise due to sub-sampling of acquired data for a given x-ray detector dimension and scan configuration relative to the first slice thickness. In a fourth example of the method optionally including one or more of the first through third examples, the trained deep neural network is trained with ground truth images generated by a super-resolution neural network configured to transform an input image with a second slice thickness to an output image with the first slice thickness, wherein the second slice thickness is larger than the first slice thickness. In a fifth example of the method optionally including one or more of the first through fourth examples, the method further comprises selecting the second slice thickness of the input image to avoid artifacts caused by sub-sampling of acquired data for the given x-ray detector dimension and the scan configuration relative to the first slice thickness. In a sixth example of the method optionally including one or more of the first through fifth examples, the method further comprises selecting the second slice thickness of the input image according to a helical pitch of a computed tomography imaging system comprising the x-ray detector during an acquisition of the input image. In a seventh example of the method optionally including one or more of the first through sixth examples, the trained deep neural network corrects high-frequency components of the three-dimensional image volume corresponding to the aliasing artifacts. In an eighth example of the method optionally including one or more of the first through seventh examples, the trained deep neural network is trained with one or more of two-dimensional, two-and-a-half dimensional, and three-dimensional images to filter image data of the three-dimensional image volume along directions perpendicular to an imaging plane formed by the x-ray detector and the x-ray source.

In another embodiment, a method comprises acquiring, with an x-ray detector, a three-dimensional image volume of a subject while the subject moves in a direction relative to an imaging plane defined by the x-ray detector and an x-ray source, reconstructing a first plurality of two-dimensional images with a first slice thickness from the three-dimensional image volume along planes perpendicular to the imaging plane, reconstructing a second plurality of two-dimensional images with a second slice thickness from the three-dimensional image volume along the planes perpendicular to the imaging plane, the second slice thickness larger than the first slice thickness, and training a deep neural network to reduce aliasing artifacts in the first plurality of two-dimensional images based on ground truth images generated from the second plurality of two-dimensional images.

In a first example of the method, training the deep neural network comprises inputting the second plurality of two-dimensional images to a second deep neural network to generate a plurality of super-resolution images with the first slice thickness, wherein the ground truth images comprise the plurality of super-resolution images, inputting the first plurality of two-dimensional images to the deep neural network to generate a plurality of corrected images, and updating parameters of the deep neural network based on a loss between the plurality of super-resolution images and the plurality of corrected images. In a second example of the method optionally including the first example, the aliasing artifacts present in the plurality of two-dimensional images arise due to sub-sampling of acquired data for a given x-ray detector dimension and scan configuration relative to the first slice thickness. In a third example of the method optionally including one or more of the first and second examples, the method further comprises selecting the first slice thickness according to a helical pitch of a computed tomography imaging system comprising the x-ray detector and the x-ray source during an acquisition of the three-dimensional image volume. In a fourth example of the method optionally including one or more of the first through third examples, the method further comprises generating the ground truth images from the second plurality of two-dimensional images by enhancing spatial resolution of the second plurality of two-dimensional images through one or more of hardware-based processing or software-based processing.

In yet another embodiment, an imaging system comprises a gantry with a bore, an x-ray source mounted to the gantry and configured to generate x-rays, an x-ray detector mounted to the gantry and configured to detect the x-rays, and a processor configured with instructions in a non-transitory memory that when executed cause the processor to: acquire, with the x-ray detector, a three-dimensional image volume of a subject while the subject moves through the bore as the gantry rotates the x-ray detector and the x-ray source around the subject, input the three-dimensional image volume to a trained deep neural network to generate a corrected three-dimensional image volume with a reduction in aliasing artifacts, and output the corrected three-dimensional image volume.

In a first example of the system, the processor is further configured with instructions in the non-transitory memory that when executed cause the processor to: reconstruct a plurality of two-dimensional images from the three-dimensional image volume along planes perpendicular to an imaging plane formed by the x-ray detector and the x-ray source; input the plurality of two-dimensional images to the trained deep neural network to generate a plurality of corrected images; and generate the corrected three-dimensional image volume from the plurality of corrected images. In a second example of the system optionally including the first example, the processor is further configured with instructions in the non-transitory memory that when executed cause the processor to: reconstruct the plurality of two-dimensional images with a first slice thickness, wherein the aliasing artifacts present in the plurality of two-dimensional images arise due to sub-sampling of acquired data for a given x-ray detector dimension and scan configuration relative to the first slice thickness. In a third example of the system optionally including one or more of the first and second examples, the trained deep neural network is trained with ground truth images generated by a super-resolution neural network configured to transform an input image with a second slice thickness to an output image with the first slice thickness, where the second slice thickness is larger than the first slice thickness. In a fourth example of the system optionally including one or more of the first through third examples, the processor is further configured with instructions in the non-transitory memory that when executed cause the processor to: select the second slice thickness of the input image to avoid sub-sampling of acquired data relative to the second slice thickness. In a fifth example of the system optionally including one or more of the first through fourth examples, the processor is further configured with instructions in the non-transitory memory that when executed cause the processor to: select the second slice thickness of the input image according to a helical pitch during an acquisition of the input image. In a sixth example of the system optionally including one or more of the first through fifth examples, the three-dimensional image volume is acquired with the helical pitch. In a seventh example of the system optionally including one or more of the first through fourth examples, the trained deep neural network corrects high-frequency components of the three-dimensional image volume corresponding to the aliasing artifacts.

As used herein, an element or step recited in the singular and proceeded with the word “a” or “an” should be understood as not excluding plural of said elements or steps, unless such exclusion is explicitly stated. Furthermore, references to “one embodiment” of the present invention are not intended to be interpreted as excluding the existence of additional embodiments that also incorporate the recited features. Moreover, unless explicitly stated to the contrary, embodiments “comprising,” “including,” or “having” an element or a plurality of elements having a particular property may include additional such elements not having that property. The terms “including” and “in which” are used as the plain-language equivalents of the respective terms “comprising” and “wherein.” Moreover, the terms “first,” “second,” and “third,” etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:

acquiring, with an x-ray detector and an x-ray source coupled to a gantry, a three-dimensional image volume of a subject while the subject moves through a bore of the gantry and the gantry rotates the x-ray detector and the x-ray source around the subject;

inputting the three-dimensional image volume to a trained deep neural network to generate a corrected three-dimensional image volume with a reduction in aliasing artifacts present in the three-dimensional image volume, wherein the trained deep neural network is trained by a super-resolution neural network configured to transform an input image with a second slice thickness to an output image with a first slice thickness, wherein the second slice thickness of the input image is selected to avoid artifacts caused by sub-sampling of acquired data for a given x-ray detector dimension and a scan configuration relative to the first slice thickness; and outputting the corrected three-dimensional image volume.

2. The method of claim 1, further comprising performing, with the trained deep neural network, two-dimensional processing of the three-dimensional image volume to filter image data of the three-dimensional image volume along directions perpendicular to an imaging plane formed by the x-ray detector and the x-ray source.

3. The method of claim 2, wherein inputting the three-dimensional image volume to the trained deep neural network to generate the corrected three-dimensional image volume comprises:

reconstructing a plurality of two-dimensional images from the three-dimensional image volume along planes perpendicular to the imaging plane formed by the x-ray detector and the x-ray source;

inputting the plurality of two-dimensional images to the trained deep neural network to generate a plurality of corrected two-dimensional images; and generating the corrected three-dimensional image volume from the plurality of corrected two-dimensional images.

4. The method of claim 3, further comprising reconstructing the plurality of two-dimensional images with the first slice thickness, wherein the aliasing artifacts present in the plurality of two-dimensional images arise due to sub-sampling of acquired data for a given x-ray detector dimension and scan configuration relative to the first slice thickness.

5. The method of claim 4, wherein the trained deep neural network is trained with ground truth images generated by the super-resolution neural network configured to transform the input image with the second slice thickness to the output image with the first slice thickness, wherein the second slice thickness is larger than the first slice thickness.

6. The method of claim 5, further comprising selecting the second slice thickness of the input image according to a helical pitch of a computed tomography imaging system comprising the x-ray detector during an acquisition of the input image.

7. The method of claim 1, wherein the trained deep neural network is trained with one or more of two-dimensional, two-and-a-half dimensional, and three-dimensional images to filter image data of the three-dimensional image volume along directions perpendicular to an imaging plane formed by the x-ray detector and the x-ray source.

8. A method, comprising:

acquiring, with an x-ray detector, a three-dimensional image volume of a subject while the subject moves in a direction relative to an imaging plane defined by the x-ray detector and an x-ray source;

reconstructing a first plurality of two-dimensional images with a first slice thickness from the three-dimensional image volume along planes perpendicular to the imaging plane;

reconstructing a second plurality of two-dimensional images with a second slice thickness from the three-dimensional image volume along the planes perpendicular to the imaging plane, the second slice thickness larger than the first slice thickness; and training a deep neural network to reduce aliasing artifacts in the first plurality of two-dimensional images based on ground truth images generated from the second plurality of two-dimensional images, wherein the trained deep neural network is trained by a super-resolution neural network configured to transform an input image with the second slice thickness to an output image with the first slice thickness, wherein the second slice thickness of the input image is selected to avoid artifacts caused by sub-sampling of acquired data for a given x-ray detector dimension and a scan configuration relative to the first slice thickness.

9. The method of claim 8, wherein training the deep neural network comprises:

inputting the second plurality of two-dimensional images to a second deep neural network to generate a plurality of super-resolution images with the first slice thickness, wherein the ground truth images comprise the plurality of super-resolution images;

inputting the first plurality of two-dimensional images to the deep neural network to generate a plurality of corrected images; and updating parameters of the deep neural network based on a loss between the plurality of super-resolution images and the plurality of corrected images.

10. The method of claim 9, further comprising generating the ground truth images from the second plurality of two-dimensional images by enhancing spatial resolution of the second plurality of two-dimensional images through one or more of hardware-based processing or software-based processing.

11. An imaging system, comprising:

a gantry with a bore;

an x-ray source mounted to the gantry and configured to generate x-rays;

an x-ray detector mounted to the gantry and configured to detect the x-rays; and a processor configured with instructions in a non-transitory memory that when executed cause the processor to:

acquire, with the x-ray detector, a three-dimensional image volume of a subject while the subject moves through the bore as the gantry rotates the x-ray detector and the x-ray source around the subject;

input the three-dimensional image volume to a trained deep neural network to generate a corrected three-dimensional image volume with a reduction in aliasing artifacts, wherein the trained deep neural network is trained by a super-resolution neural network configured to transform an input image with a second slice thickness to an output image with a first slice thickness, wherein the second slice thickness of the input image is selected to avoid the aliasing artifacts caused by sub-sampling of acquired data for a given x-ray detector dimension and a scan configuration relative to the first slice thickness; and output the corrected three-dimensional image volume.

12. The system of claim 11, wherein the processor is further configured with instructions in the non-transitory memory that when executed cause the processor to:

reconstruct a plurality of two-dimensional images from the three-dimensional image volume along planes perpendicular to an imaging plane formed by the x-ray detector and the x-ray source;

input the plurality of two-dimensional images to the trained deep neural network to generate a plurality of corrected images; and generate the corrected three-dimensional image volume from the plurality of corrected images.

13. The system of claim 12, wherein the processor is further configured with instructions in the non-transitory memory that when executed cause the processor to:

reconstruct the plurality of two-dimensional images with the first slice thickness, wherein the aliasing artifacts present in the plurality of two-dimensional images arise due to sub-sampling of acquired data for the given x-ray detector dimension and the scan configuration relative to the first slice thickness.

14. The system of claim 13, wherein the processor is further configured with instructions in the non-transitory memory that when executed cause the processor to:

select the second slice thickness of the input image to avoid sub-sampling of acquired data relative to the second slice thickness.

15. The system of claim 14, wherein the processor is further configured with instructions in the non-transitory memory that when executed cause the processor to:

select the second slice thickness of the input image according to a helical pitch during an acquisition of the input image.

16. The system of claim 15, wherein the three-dimensional image volume is acquired with the helical pitch.

17. The system of claim 16, wherein the trained deep neural network corrects high-frequency components of the three-dimensional image volume corresponding to the aliasing artifacts.

18. The system of claim 11, wherein the imaging system is a computed tomography imaging system comprising the x-ray detector during an acquisition of the three-dimensional input image volume.

19. The system of claim 11, wherein the imaging system is configured to select a model according to a pitch value comprising the value of the helical pitch.

20. The system of claim 11, wherein the model is selected based on a speed of a table and a rotation of the gantry, and wherein a plurality of deep neural networks are each trained for a respective helical pitch value.

* * * * *